(12) United States Patent
Raouf

(10) Patent No.: US 11,344,667 B1
(45) Date of Patent: May 31, 2022

(54) PERSONAL HYGIENE DEVICE

(71) Applicant: Paymon Raouf, Las Vegas, NV (US)

(72) Inventor: Paymon Raouf, Las Vegas, NV (US)

(\*) Notice: Subject to any disclaimer, the term of this patent is extended or adjusted under 35 U.S.C. 154(b) by 48 days.

(21) Appl. No.: 16/891,053

(22) Filed: Jun. 3, 2020

(51) Int. Cl.
*A61M 3/02* (2006.01)
*A61M 3/06* (2006.01)

(52) U.S. Cl.
CPC ........ *A61M 3/0225* (2013.01); *A61M 3/0233* (2013.01); *A61M 3/06* (2013.01); *A61M 2210/1067* (2013.01)

(58) Field of Classification Search
CPC .............. A61M 3/0225; A61M 3/0233; A61M 3/0279; A61M 3/0216; A61M 3/0262; A61M 3/02; A47K 13/06; A47K 13/14
See application file for complete search history.

(56) References Cited

U.S. PATENT DOCUMENTS

| | | | | |
|---|---|---|---|---|
| 653,842 | A * | 7/1900 | Brown | A61M 3/0225 604/182 |
| 2,534,082 | A * | 12/1950 | Turley | A61M 3/0225 604/182 |
| 3,671,981 | A * | 6/1972 | Smith | A47K 13/005 4/245.7 |
| 5,619,757 | A * | 4/1997 | Baratta | A47K 13/06 4/239 |
| 2007/0276268 | A1 * | 11/2007 | Edgerley | F16K 15/202 600/498 |
| 2014/0276631 | A1 * | 9/2014 | Gilman | A61M 3/0279 604/514 |
| 2015/0335529 | A1 * | 11/2015 | Andersson | A61J 1/1475 206/438 |
| 2019/0022301 | A1 * | 1/2019 | Fields | A61M 39/28 |

\* cited by examiner

*Primary Examiner* — Bhisma Mehta
*Assistant Examiner* — Phoebe Anne Staton
(74) *Attorney, Agent, or Firm* — Lewis Roca Rothgerber Christie LLP

(57) ABSTRACT

A personal hygiene device comprises a tubular body constructed of a substantially watertight flexible material. The tubular body defines a cavity. An opening in the tubular body provides access to the cavity, which opening is selectively closable to create a watertight seal. A spray member, having a first end and a second end, is operatively connected to the tubular body at the first end. A channel in the spray member extends from the first end to the second end. The channel is exposed to the cavity at the first end. The second end of the spray member has openings that are exposed to the channel. Material in the cavity can travel from the cavity through the channel in the spray member, and exit through the openings in its second end. An adjusting means is selectively operable to control the amount of material that flows into the channel.

18 Claims, 3 Drawing Sheets

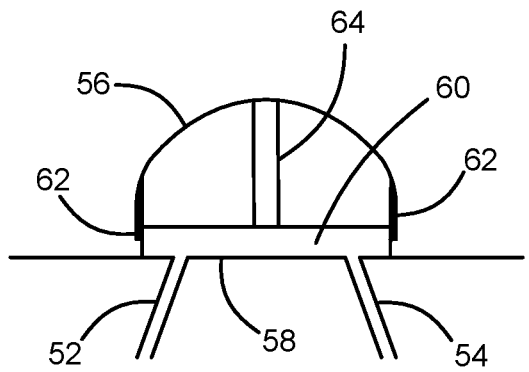
FIG. 7b
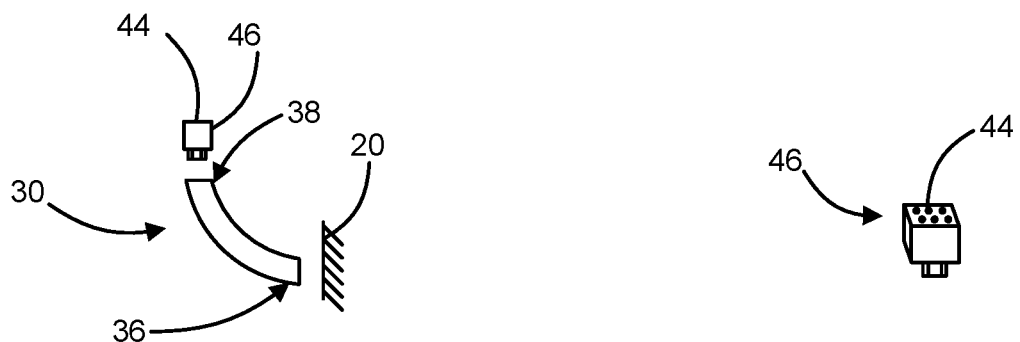
FIG. 8a
FIG. 8b
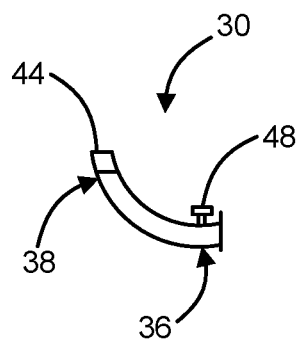
FIG. 9

PERSONAL HYGIENE DEVICE

FIELD OF INVENTION

This invention concerns personal hygiene devices, and more specifically, to a personal irrigation device to irrigate particular areas of the body.

BACKGROUND

Some patients suffer from a medical condition called piles, or more commonly referred to as hemorrhoids. This condition is often uncomfortable and painful for patients. Patients sometimes seek relief by irrigating the particular location with a liquid such as water, which delivers a soothing sensation in the affected area.

Such irrigation procedure can be performed in various ways. Some devices provide a small tub which the patient fills with water and sits in it, whereby the water helps soothe the patient's symptoms. However, sitting in such water can be unhygienic as the water is exposed to the patient's crotch area and anal area while the patient sits in that water.

Other devices provide a running source of water, fed through a water-supply means such as a hose connected to a faucet, that the patient may use to spray the afflicted areas on their body. However, such devices have drawbacks. They require an active source of water supply, which delivers water with at least some pressure, and which the device must remain connected to during use. This restricts the distance the device and the patient can be from the source of water during use. Further, the supply means, or hose, itself can be cumbersome for the patient to maneuver to reach difficult-to-reach areas on their body and be able to properly irrigate them.

People also have a need sometimes to irrigate other particular parts of their bodies. These include douching the vaginal area for females, performing enemas, cleaning the anal area after a bowel movement, etc. Known devices offer a solution to one or more of these requirements, but they do not provide one device or one general solution to serve each of these needs.

Accordingly, there is a need for a personal irrigation device that does not require a live or pressurized source of water that is active during use, which is convenient for a patient to use and maneuver for particular difficult-to-reach areas of their body, which is portable, and which can be used for multiple purposes for irrigating areas of their body.

COPYRIGHT NOTICE

© 2020 Paymon Raouf. The disclosure in this patent document includes material that is subject to copyright protection. The copyright owner agrees to fair use by facsimile reproduction of the patent document or of the patent disclosure as it appears in the U.S. Patent and Trademark Office's files and records. Other than that, all copyright rights to the disclosure herein are expressly reserved. 37 CFR § 1.71(d).

SUMMARY OF THE INVENTION

The present invention comprises a device with a tubular body. In one embodiment the tubular body is shaped generally as a toroid. In that embodiment the tubular body corresponds generally to the shape of a common household toilet, whereby the tubular body's circumference has a generally oval shape that defines a hollow opening. The tubular body itself defines a cavity inside the tubular body that runs substantially throughout the interior of the tubular body. The tubular body is substantially watertight, whereby the cavity therein can hold a liquid, such as water, without a significant risk of leakage.

The device's tubular body is constructed of a flexible material, such as rubber or a waterproof fabric, whereby it can expand and contract to accommodate a volume of material, such as a liquid, in the cavity, and can be folded for portability.

The device's tubular body has an opening means that provides access to the cavity. A user may selectively open the opening and fill the cavity with a desired material, such as water. After filling the cavity, the user may selectively close the opening to form a substantially watertight seal to hold the material inside without any significant risk of leakage.

A spray member, such as a nozzle, is operatively connected to the tubular body. The spray member has an elongated body with at least two opposite ends. The spray member is operatively connected at one end to the device's body. The elongated body of the spray member extends from the device's body, preferably at a predetermined angle. The spray member has a channel in its elongated body, which runs between two opposite ends of the spray member. The channel allows the flow of a material, such as a liquid, through the spray member's elongated body from one end to an opposite end. The channel in the spray member is operatively connection to the cavity in the device's tubular body, which allows a material in the cavity, such as a liquid, to flow from the cavity to the channel in the spray member. The opposite end of the spray member has at least one opening through which the material can be expelled. This allows the material in the cavity in the device's tubular body to flow through the elongated body of the spray member to the opening at the opposite end of the spray member, and exit from the opening.

In one embodiment an adjustable member is operatively connected to the device's body that can be selectively operated to control the amount of material that exits from the cavity to the channel in the spray member. This allows a user to control the amount and pressure of the material that exits from the opening in an opposite end of the spray member.

One skilled in the art will appreciate that the amount of pressure applied on the flexible body will directly correspond to the pressure at which the material will exit the opening at an opposite end of the spray member. Therefore the greater the amount of pressure applied on the flexible body of the device, the stronger the pressure at which the material in the cavity will flow into the channel in the spray member, and consequently, the pressure at which the material will exit the opening at an opposite end of the spray member. If enough pressure is applied on the flexible tubular body, the material in the cavity, such as water, will exit the opening in the spray member in the form of a stream. If there are a plurality of openings in the spray member, such pressure will cause the material, such as water, to be expelled from the spray member in the form of a spray. This material will be directed at a particular area on the user's body.

BRIEF DESCRIPTION OF THE FIGURES

The invention can be better understood with reference to the figures. In these figures like reference numerals designate corresponding parts throughout the different figures and views.

FIG. 7b is a sectional view of the adjusting means of FIG. 7a with the adjusting means in an open position.

FIG. 8a is an exploded view of one embodiment of the spray member of FIG. 5.

FIG. 8b is a perspective view of a detachable member in the spray member of FIG. 8a.

FIG. 9 is a side view of the spray member of FIG. 5.

DETAILED DESCRIPTION

The systems, methods and apparatus of the present invention are described below with reference to the figures. The description and figures are for illustrative purposes only, they do not limit the true scope and spirit of the present invention. The true spirit and scope of the invention is evidenced by all parts of the disclosure herein, including but not limited to the Summary, the Figures, the Detailed Description, and the Claims, along with equivalents thereof.

Figure 1:
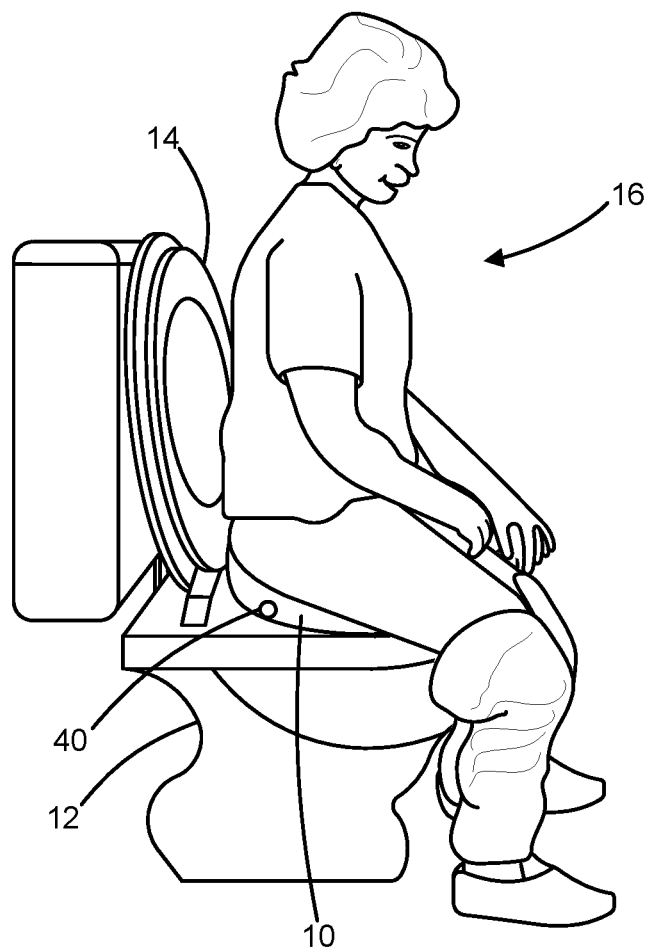
FIG. 1 shows a person using a device of the present invention on a toilet.

Referring to FIG. 1, a device 10 in accordance with the present invention is shown in use by a person 16 on a common household toilet 12. In this embodiment device 10 is implemented on the top of the toilet 12. In one embodiment, device 10 is removably placed on top of the toilet's 12 rim, or atop a toilet seat 14. In alternate embodiments, device 10 may be implemented integrally with a toilet or another platform suitable for use with the present invention. Or device 10 may be removably placed on another platform suitable for use with device 10.

Figure 2:
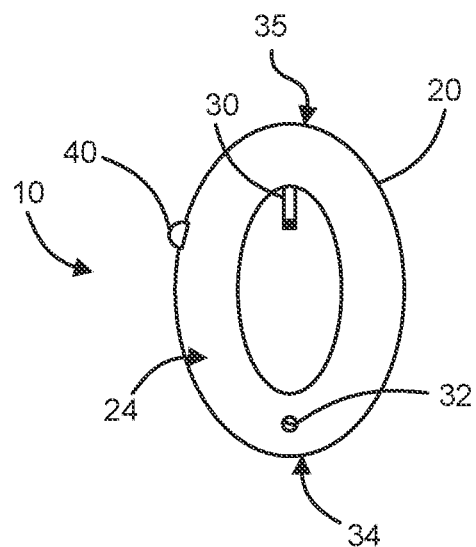
FIG. 2 is a top view of the device of FIG. 1.

Referring to FIG. 2, a top view of device 10 is shown. Device 10 has a tubular body 20. In the embodiment shown, tubular body 20 is generally a toroid that is oval in shape. However, it is anticipated that tubular body 20 in other embodiments may have a non-toroid shape, such as square, rectangular, circular, or the like, without deviating the spirit and scope of the present invention. All such embodiments, therefore, are anticipated and are intended to be included in the present claims.

Tubular body 20 is preferably constructed of a flexible material whereby tubular body 20 can expand or contract, and device 10 can be folded for packaging, storage, portability, or other purposes. The flexible material of tubular body 20 may be any material such as rubber, a flexible fabric like an elastic synthetic material, or the like, which has substantially watertight characteristics. Further, the flexible material should be of a thickness and strength sufficient to withstand the pressure created by a material, such as a liquid, inside tubular body 20. Further, the flexible material of tubular body 20 must be able to withstand additional pressure that may be applied on the material inside tubular body 20, such as pressure resulting from the bodyweight of a user sitting on device 10. Such strong flexible materials that are substantially watertight are known in the art.

Device 10 has a hollow interior, whereby the flexible material of tubular body 20 defines a cavity 22 inside tubular body 20. Cavity 22 preferably runs substantially throughout the circumference of the tubular body 20. In the embodiment shown, cavity 22 will have a generally toroid shape corresponding to the generally toroid shape of tubular body 20. However, it is anticipated that other embodiments of device 10 will have a different shaped cavity 22 inside tubular body 20 without deviating from the spirit and scope of the present invention.

Figure 4:
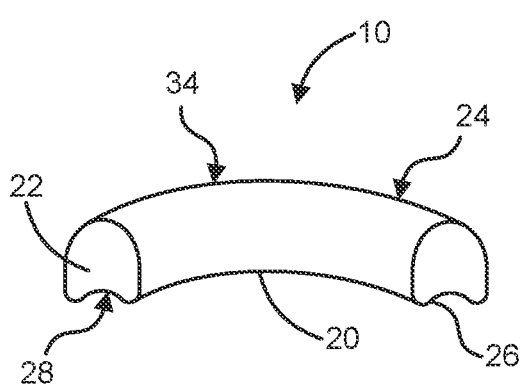
FIG. 4 is a sectional view of the device of FIG. 1.

FIG. 4 shows a sectional view of device 10. In the embodiment shown, tubular body 20 has a top 24, which is preferably curved in shape. Such curved shape helps provide a more comfortable seat for a person sitting on the top 24 of device 10, and it contributes to maximizing a volume, or capacity, of the cavity 22 inside tubular body 20. The height of the tubular body is approximately five inches in the embodiment shown in FIG. 4. However, it is anticipated that top 24 of tubular body 20 may have a different shape or size without deviating from the spirit and scope of the present invention.

As shown in the sectional view of device 10 in FIG. 4, tubular body 20 has a bottom 26. Bottom 26 of tubular body 20 preferably has an indentation 28. In the embodiment shown in FIG. 4, indentation 28 is implemented towards the middle of bottom 26. Indentation 28 may be of any shape, and will vary from one embodiment to another. In the embodiment shown, indentation 28 has a gently curved shape.

Figure 3:
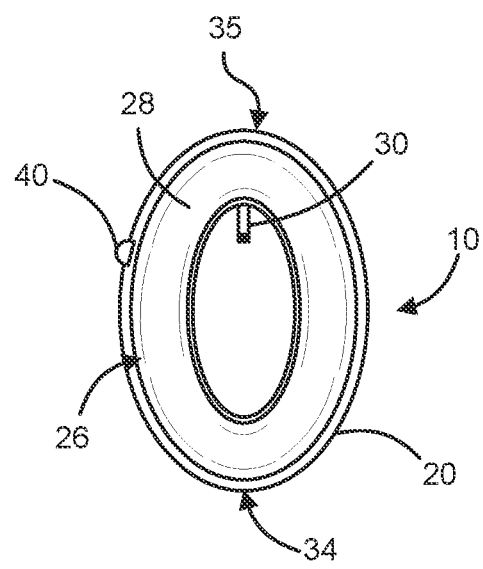
FIG. 3 is a bottom view of the device of FIG. 1.

Indentation 28 preferably runs along the entire periphery of the bottom 26 of the tubular body 20 of device 10. This is shown in FIG. 3, which shows a bottom view of device 10. As one skilled in the art will appreciate, indentation 28 will help position the device 10 more stably on a platform, such as on a toilet rim, while in use.

Device 10 has an opening means 32 operatively implemented in the tubular body 20. In the embodiment shown in FIG. 2, opening means 32 is implemented at the top 24 towards a front portion 34 of the device 10. However, it is anticipated that opening means 32 may be implemented elsewhere in tubular body 20 in alternate embodiments, and may be implemented anywhere practical in tubular body 20. In one embodiment, opening means 32 is implemented at a rear portion 35 of device 10.

In one embodiment, opening means 32 comprises a circular shaped plastic or metallic lid that threadedly engages with corresponding threading in tubular body 20. A user may selectively implement the lid on the tubular body 20 by twisting the lid and engaging the corresponding threads between the lid and tubular body 20. Implementing the lid on tubular body 20 preferably forms a substantially watertight seal between the lid and tubular body 20. A user may similarly selectively remove the lid by twisting it and separating its threaded engagement with the corresponding threads in tubular body 20.

In an alternate embodiment, opening means 32 comprises a lid that is designed to engage and connect with a corresponding receptacle in tubular body 20 by resistively sliding the lid relative to the corresponding receptacle. In such embodiment a user may selectively slide the lid into its corresponding receptacle in the tubular body 20 to operatively plug the opening means 32 frictionally closed in a substantially watertight manner. Vice versa, the user may selectively slide the lid out of its corresponding receptacle in opening means 32 to remove the lid from the opening means 32.

In one embodiment, opening means 32 comprises a rubber or silicone ring to help achieve a substantially watertight engagement.

One skilled in the art will recognize that opening means 32 may be designed and implemented in tubular body 20 in a number of ways. All such variations and embodiments are anticipated as they are consistent with the spirit and scope of the present invention.

Opening the opening means 32, such as by removing the lid in the embodiment shown in FIG. 2, exposes the cavity 22 inside tubular body 20. A user may pour a material, such as a liquid, like water, in cavity 22 through opening means 32. Subsequently reengaging the lid with tubular body 20 to close opening means 32 restricts the material within cavity 22 due to the substantially watertight material of tubular body 20 and the substantially watertight seal at opening means 32.

Figure 5:
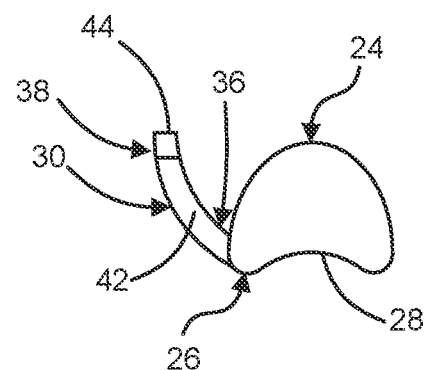
FIG. 5 is a partial view of a spray member operatively connected to the device of FIG. 1.

Referring to FIG. 5, a partial view of a spray member 30 operatively connected to device 10 is shown. Spray member 30 is connected to a rear portion 35 of device 10, preferably towards a bottom 26 of device 10. Spray member 30 is preferably operatively connected to tubular body 20 in a substantially watertight manner.

Spray member 30 has an elongated body, with at least two opposite ends, first end 36 and second end 38. Spray member 30 is operatively connected to tubular body 20 at its first end 36 in a substantially watertight manner.

In one embodiment, spray member 30 is integrally constructed with the tubular body at its first end 36. In alternate embodiments, spray member 30 may be designed to engage with a corresponding means in tubular body 20, whereby a user may selectively remove or implement spray member 30 on tubular body 20.

In one embodiment, spray member 30 has threading at first end 36 designed to threadedly engage with corresponding threads in tubular body 20. In such embodiment, a user may selectively threadedly implement or remove spray member 30 from tubular body 20.

In another embodiment, first end 36 is designed to cooperatively engage and connect with a corresponding receptacle in tubular body 20 by resistively sliding the two relative to each other. In such embodiment a user may selectively slide spray member 30 into its corresponding receptacle in tubular body 20 to operatively connect spray member 30 with tubular body 20 and frictionally hold spray member 30 in place. Vice versa, the user may selectively slide spray member 30 out of its corresponding receptacle in tubular body 20 to remove spray member 30 from tubular body 20.

One skilled in the art will recognize that spray member 30 may be designed and implemented to operatively connect with tubular body 20 in a number of ways to achieve a substantially watertight connection. All such variations are anticipated and are intended to be covered by the present claims as they are consistent with the spirit and scope of the present invention.

Spray member's 30 elongated shaped body extends from tubular body 20 as shown in FIGS. 2 and 3. In one embodiment, the elongated body of the spray member 30 is slightly curved. However, in alternate embodiments the elongated body of spray member 30 may have a different shape, such as a straight shape, provided that its implementation conforms with the spirit of the present invention. All such embodiments are anticipated and are intended to be covered by the present claims.

Spray member 30 has a channel 42 that runs from first end 36 to second end 38. Channel 42 is directly exposed to cavity 22 in tubular body 20. In one embodiment channel 42 is a hollow tube. In an alternate embodiment, the interior of the spray member 30 is hollow, whereby the hollow elongated body of spray member 30 forms a channel 42 that extends from first end 36 to second end 38. In another emodiment, a tube runs from first end 36 to second end 38, which comprises a channel 42. One skilled in the art will recognize that channel 42, extending from first end 36 to second end 38, may be designed or implemented in a number of ways in different embodiments of the present invention. All such implementations and embodiments are anticipated, and are intended to be covered by the present claims.

Spray member 30 has at least one opening 44 at second end 38. Opening 44 is exposed to channel 42 in spray member 30. In alternate embodiments, spray member 30 has a plurality of openings 44 at second end 38, with the openings 44 exposed to channel 42 in spray member 30. The size of openings 44 may vary from one embodiment to another, but will typically depend on the particular purpose that specific embodiment is intended to serve for a user. As shown in FIG. 8b, detachable member 46 in one embodiment has more than two openings 44, and the openings 44 in that embodiment are disposed adjacently relative to each other, or in other words they are disposed relatively close to each other. Further as shown in FIG. 8b, in one embodiment the openings 44 are disposed relatively planarly with respect to each other, i.e. more than two openings 44 are disposed in the same two-dimensional plane. All such embodiments, with varying numbers and sizes of openings 44, are anticipated and are intended to be covered by the present claims.

In one embodiment, openings 44 are integrally implemented in spray member 30 at second end 38. In an alternate embodiment, second end 38 includes a detachable member 46 that is operatively connected to spray member 30 at second end 38. In such embodiment, a user may selectively attach or detach the detachable member 46 from second end 38 of spray member 30. Further in such embodiment, openings 44 are exposed to channel 42 in spray member 30.

In one such embodiment, detachable member 46 may have threading that is designed to threadedly engage with corresponding threads in second end 38 of spray member 30. In such embodiment, a user may selectively threadedly implement and remove detachable member 46 from second end 38 of spray member 30.

In an alternate embodiment, detachable member 46 is designed to engage and connect to second end 38 via a corresponding receptacle in second end 38 by resistively sliding detachable member 46 relative to second end 38 of spray member 30. In such embodiment a user may selectively slide the detachable member 46 into its corresponding receptacle in second end 38 to operatively connect the detachable member 46 to spray member 30. Vice versa, the user may selectively slide the detachable member 46 out of its corresponding receptacle in second end 38 of spray member 30 to remove the detachable member 46 from spray member 30.

One skilled in the art will recognize that detachable member 46 may be designed and implemented to operatively connect with spray member 30 at its second end 38 in a number of ways. All such variations and embodiments are anticipated as they are consistent with the spirit and scope of the present invention, and are intended to be covered by the present claims.

One skilled in the art will appreciate that having the option to selectively choose between different detachable members 46 for use with device 10 will facilitate a user's ability to selectively choose a particular detachable member 46 that is designed to serve a particular function or need, and then to selectively replace it with a different detachable member 46 to reuse device 10 to serve a different particular function or need. For example, for one particular need the user may desire a detachable member 46 that has numerous smaller sized holes, but for another particular need, the user may desire a detachable member 46 that has only a few holes that are larger in size.

Spray member 30 may be designed in different ways and from different materials to serve different needs for users. In one embodiment, spray member 30 is a tube constructed of a flexible material, such as rubber or silicone for example. The tube is preferably of a length whereby it may be flexed and maneuvered by a user while using device 10. This embodiment may serve female users who use device 10 for douching purposes, whereby the flexible maneuverability of spray member 30 will facilitate the placement and direction of second end 38 as desired by a user to comfortably accomplish the douching process.

In another embodiment, spray member 30 is constructed of inter-connectable separate parts that may be connected serially. In such embodiment the channel 42 runs continuously in series through each of the inter-connected parts, whereby a material can flow continuously through each of the inter-connected separate parts without obstruction. One skilled in the art will appreciate that a user may remove or add one or more of the parts to shorten or lengthen the length of spray members 30. This feature will allow a user to selectively adjust the position and performance of spray member 30 relative to their body by adding or removing said parts.

The construction of device 10 allows a material in cavity 22, such as a liquid like water, to flow into channel 42 of spray member 30 at the first end 36 of spray member 30. Such material flowing through channel 42 will exit through the openings 44 at second end 38 of spray member 30. The pressure at which this material, or liquid, will exit openings 44 will be a direct function of the amount of pressure at which the material enters channel 42 from cavity 22. The pressure at which the material enters channel 42 from cavity 22 will be a direct function of the amount of pressure on the material in cavity 22. Thus, the greater the pressure on the material in cavity 22, the greater the force with which it will be expelled from openings 44.

If the pressure on the material in cavity 22 is strong enough, the material in cavity 22 will be expelled from openings 44 in the form of a stream. Accordingly, if there are only one or two openings 44 at second end 38, the material will be expelled at a greater pressure with one or two strong streams of the material. This may be important, for example, for a person using the device 10 for an enema. On the other hand, if there are several openings 44 at end 38, the material will be expelled in the form of several streams, but at a comparatively lesser pressure each. This may be important, for example, for a person using device 10 to irrigate an area afflicted with hemorrhoids, or using device 10 as a bidet. In an alternate embodiment with fewer openings 44 at second end 38, with each opening 44 of a smaller size, the material will be expelled in the form of several streams having lesser pressure. This may be important, for example, for a person using device 10 for douching.

Accordingly, one skilled in the art will recognize that the functioning of device 10, and the particular purpose it serves for a particular user, can be adjusted by varying the number of openings 44 and their respective size. Several needs for a user can be served with one device 10 by varying the number of openings 44 and their respective size. All such variations and embodiments are anticipated, and are intended to be covered by the present claims.

FIG. 9 shows one embodiment of spray member 30 that has a valve 48 which a user may selectively operate to close or open channel 42 in spray member 30. A user may thus selectively operate valve 48 to stop the flow of material, such as a liquid like water, through channel 42, or on the other hand, operate it to allow and control the flow of material through channel 42. Valves to serve such function of opening, closing, and controlling flow of material through a channel, or through a pipe, are well known.

Figure 6:
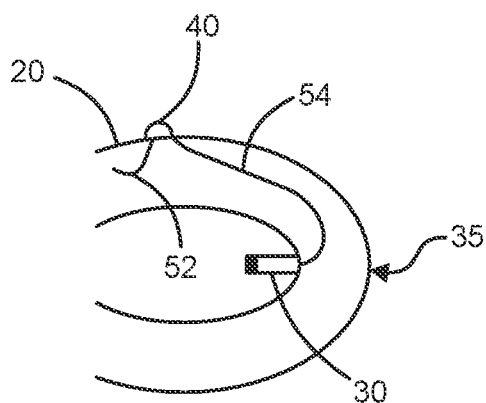
FIG. 6 is a partial view of an adjusting means and some of its associated components in the device of FIG. 1.

In one embodiment, device 10 includes an adjusting means 40 as shown in FIGS. 2, 3, and 6. Adjusting means 40 allows a user to adjust the amount of material that flows from cavity 22 to channel 42 in spray member 30. One skilled in the art will recognize that as the amount of material flowing from cavity 22 to channel 42 is increased, the material will be expelled from openings 44 with greater pressure. Accordingly, using adjusting means 40 a user will be able to adjust the amount of force with which material is expelled from openings 44 to suit their specific preference and comfort level, and serve the specific purpose for which they are using device 10.

FIG. 6 shows a partial view of one embodiment of adjusting means 40 and components associated with it. In this embodiment adjusting means 40 is implemented on tubular body 20. Adjusting means 40 is preferably implemented on the right side of the device 10 as shown in FIGS. 2, 3, and 6. Such implementation allows a right-handed person to selectively operate adjusting means 40 with their right hand while using device 10. However, it is anticipated that adjusting means 40 may be implemented anywhere on tubular body 20, such as on the left side of device 10, without deviating from the spirit and scope of the present invention.

Referring to FIG. 6, a first tube 52 having two ends is operatively connected at one end to adjusting means 40. First tube 52 is a tube known in the art that has a hollow interior that allows a material, such as air or a liquid, to flow through its hollow interior. The other end of first tube 52 extends into cavity 22 of device 10 and is freely situated there, preferably near the bottom 26 of device 10 as shown in FIG. 6.

Referring to FIG. 6, a second tube 54 having two ends is operatively connected at one end to adjusting means 40. Second tube 54 is a tube known in the art that has a hollow interior that allows a material, such as air or a liquid, to flow through its hollow interior. The other end of second tube 54 is operatively connected to first end 36 of spray member 30. In this embodiment, second tube 54 is connected in a substantially watertight manner to channel 42, whereby only material traveling through second tube 54 will enter channel 42.

In this configuration, material from cavity 22 will travel via first tube 52, through adjusting means 40, through second tube 54, into channel 42 at first end 36 of spray member 30. The amount of material, such as water, entering channel 42 of spray member 30 and exiting from openings 44 can thus be controlled by selectively operating adjusting means 40.

Figure 7A:
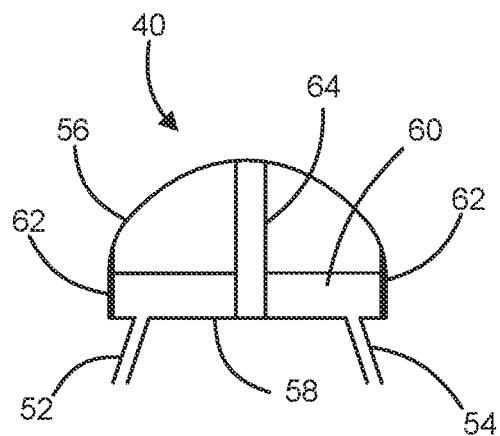
FIG. 7a is a sectional view of the adjusting means of FIG. 6 with the adjusting means in a closed position.

Adjusting means 40 can be any means known in the art for controlling the amount of flow of a material such as a liquid. One embodiment of adjusting means 40 is shown in FIGS. 7a and 7b. A dome-shaped cap 56 is operatively connected to a base 58 via corresponding threads 62 on cap 56 and on base 58. Base 58 comprises a chamber 60 that is exposed to first tube 52 on one side and to second tube 54 on another side. Material may flow from first tube 52 to second tube 54 via chamber 60.

In this embodiment, cap 56 can be rotated, or twisted, to tighten it to base 58. In this position, which is depicted in FIG. 7a, a pin 64 attached to cap 56 extends through chamber 60 and obstructs the flow of material, or liquid, through chamber 60. In this closed position, no material, or liquid, will travel from first tube 52 to second tube 54, and therefore no material, or liquid, will flow to channel 42.

Cap 56 can be rotated in an opposite direction, whereby threads 62 will cause cap 56 to move away from base 58. Pin 64 will move with cap 56, and create an opening in chamber 60. Such opening in chamber 60 will increase as cap 56 is rotated further. Material, or liquid, will then begin flowing through chamber 60, i.e. from first tube 52 to second tube 54. One skilled in the art will appreciate that as the cap 56 is rotated, it will move away more and more from base 58. Along with cap 56, pin 64 will move away from base 58 more and more, thereby increasing the opening in chamber 60. This in turn allows more material, or liquid, to flow through chamber 60, i.e. from first tube 52 to second tube 54.

Cap 56 can be rotated until pin 64 is fully withdrawn from chamber 60. This position of the cap 56 and pin 64 is depicted in FIG. 7b. In this position, adjusting means 40 allows the maximum possible material, or liquid, flow through chamber 60, i.e. from first tube 52 to second tube 54.

By operating cap 56, i.e. by rotating it in a clockwise or counter-clockwise direction, a user can adjust the amount and pressure of the material that enters channel 42, in spray member 30, to be expelled through openings 44. Increasing the amount of material flow through chamber 60 will increase the pressure of the material being expelled from openings 44, and vice versa.

A user may fill cavity 22 in device 10 with a material, such as water, via opening means 32. Device 10 can then be placed on a platform such as on the top of a toilet. A user can sit on the device 10. The bodyweight of the user will apply pressure on the flexible tubular body 20 of device 10, which in turn will apply pressure on the material, or liquid, in cavity 22 in tubular body 20. This pressure will force the material, or liquid, in cavity 22 to travel via first tube 52, through adjusting means 40, through second tube 54, to channel 42 in spray member 30. The user may adjust the amount and pressure of the flow of this material, or liquid, via adjusting means 40 as the user's bodyweight puts continuous pressure on the material, or liquid. The material, or liquid, then exits openings 44 in spray member 30 with a pressure corresponding to the user's operation of adjusting means 40.

The user's bodyweight will continuously apply pressure on the material, or liquid, in cavity 22 as the material, or liquid, is expelled via openings 44. This process will continue until substantially most of the material, or liquid, in cavity 22 has been expelled via openings 44.

The position and angle of spray member 30 can be implemented in device 10 in accordance with the the angle at which the stream of material, or liquid, is desired to be expelled from openings 44. In this regard, different spray members 30 can be utilized interchangeably with device 10 to serve different needs and purposes for a user by providing different angles of expulsion from spray member 30, different numbers of openings 44 in spray member 30, different distances between spray member 30 and a user's body, and different sizes of openings 44 in spray member 30. Similarly, having interchangeable detachable members 46 for spray member 30 can further, or alternatively, help accomplish that same goal as different detachable members may provide different angles of expulsion from spray member 30, different sizes and lengths of spray member 30, different numbers of openings 44 in detachable member 46, and different sizes of openings 44 in detachable member 46.

Although the devices, systems, apparatus and methods have been described and illustrated in connection with certain embodiments, variations and modifications will be evident to those skilled in the art. Such variations and modifications may be made without departing from the spirit and scope of the present disclosure, and are therefore anticipated. The description and teachings herein are thus not to be limited to the precise details of methodology or construction set forth because variations and modification are intended to be included in the spirit and scope of the present disclosures and teachings.

I claim:

1. A personal hygiene device, comprising:
   a tubular body, wherein:
      said tubular body is constructed of a flexible material,
      said flexible material is substantially watertight,
      said tubular body has a top and a bottom; and
      said tubular body defines a cavity inside said tubular body between said top and bottom, said cavity having a height between said top and bottom, said tubular body has a toroid shape with a circumference;
   the bottom of said tubular body comprises an indentation along the entire circumference of said tubular body, said indentation having a depth, an inner edge, and an outer edge, wherein:
      the depth of said indentation at a location of said tubular body is less than the height of said cavity at that location,
      said inner edge has a concave cross section, said outer edge has a concave cross section, and the concave cross section of the inner edge is similar to the concave cross section of the outer edge;
   an opening means in said tubular body, wherein
      said opening means can be selectively opened for access to said cavity, and
      said opening means can be selectively closed to create a substantially watertight seal at said opening means;
   a spray member operatively connected to said tubular body, wherein
      said spray member has a first end and a second end,
      said spray member is operatively connected to said tubular body at said first end,
      said spray member comprises a channel that extends from the first end of said spray member to the second end of said spray member,
      said channel is exposed to the cavity, and
      said operative connection between said spray member and said tubular body is substantially watertight; and
   an opening in said second end of said spray member, wherein said opening in said second end of said spray member is exposed to said channel in said spray member.

2. The personal hygiene device of claim 1, wherein
   the circumference of said tubular body conforms to the circumference of a platform,
   the personal hygiene device is positioned on said platform, and
   a material in said cavity can travel from said cavity through said channel in said spray member, and exit through the opening in the second end of said spray member.

3. The personal hygiene device of claim 2, wherein:
   the circumference of said tubular body has an oval shape, and
   said platform is a toilet.

4. The personal hygiene device of claim 1, further comprising a valve operatively connected to said spray member, wherein said valve can be selectively operated to open or close said channel in said spray member.

5. The personal hygiene device of claim 1, further comprising a plurality of openings in the second end of said spray member, wherein:
   said plurality of openings are exposed to the channel in said spray member, and
   said spray member is selectively removable from said tubular body.

6. The personal hygiene device of claim 1 further comprising an adjusting means operatively connected to said tubular body, wherein:
   a material in said cavity can travel from said cavity through said channel in said spray member, and exit through the opening in the second end of said spray member, and
   said adjusting means comprises a mechanism to selectively adjust an amount of material in said cavity that travels through said channel in said spray member.

7. The personal hygiene device of claim 6, wherein said mechanism comprises:
   an inlet for the material in said cavity to flow into said mechanism, and
   an outlet for said material to flow from said mechanism to the channel in said spray member; wherein
   said mechanism can be selectively operated to adjust an amount of material in said cavity that travels from said inlet to said outlet.

8. The personal hygiene device of claim 7, further comprising:
   a pin operatively connected to said adjusting means that operatively obstructs the material in said cavity that travels from said inlet to said outlet, wherein
   said inlet comprises an inlet tube with a first end and a second end, wherein the first end of said inlet tube is connected to said adjusting means and the second end of said inlet tube extends into said cavity, and
   said outlet comprises an outlet tube with a first end and a second end, wherein the first end of said outlet tube is connected to said adjusting means and the second end of said outlet tube is operatively connected to the channel in said spray member, wherein
   an amount of material in said cavity that travels from said inlet to said outlet can be selectively adjusted by operating said adjusting means to vary said pin's obstruction of the travel of the material.

9. The personal hygiene device of claim 1, further comprising a detachable member operatively connected to said spray member at the second end of said spray member, wherein:
   said detachable member is selectively attachable and selectively detachable from the second end of said spray member;
   said detachable member has an opening; and
   said opening in said detachable member is exposed to the channel in said spray member.

10. A method for irrigating an area on a user's body with a personal hygiene device, comprising:
    putting a material in said hygiene device, and
    applying pressure on said hygiene device, wherein said hygiene device comprises:
      a tubular body, wherein
        said tubular body is constructed of a flexible material,
        said flexible material is substantially watertight,
        said tubular body has a top and a bottom;
      said tubular body defines a cavity inside said tubular body between said top and bottom, said cavity having a height between said top and bottom,
      said tubular body has a toroid shape with a circumference;
    the bottom of said tubular body comprises an indentation along the entire circumference of said tubular body,
      said indentation having a depth, an inner edge, and an outer edge, wherein
      the depth of said indentation at a location of said tubular body is less than the height of said cavity at that location, and
      said inner edge has a concave cross section, said outer edge has a concave cross section, and the concave cross section of the inner edge is similar to the concave cross section of the outer edge;
      an opening means in said tubular body, wherein
        said opening means can be selectively opened for access to the cavity in said tubular body, and
        said opening means can be selectively closed to create a substantially watertight seal at said opening means; and
    a spray member operatively connected to said tubular body, wherein:
      said spray member has a first end and a second end,
      said spray member is operatively connected to said tubular body at the first end of said spray member,
      said spray member comprises a channel that extends from the first end of said spray member to the second end of said spray member,
      said channel is exposed to said cavity at the first end of said spray member, and
      said operative connection between said spray member and said tubular body is substantially watertight; wherein
      the second end of said spray member has an opening, and
      said opening in the second end of said spray member is exposed to the channel in said spray member, and
      said material put in the hygiene device is put in said cavity, and
      said material can travel from said cavity through the channel in said spray member, and exit through the opening in the second end of said spray member.

11. The method of claim 10, further comprising:
    placing the personal hygiene device on a platform,
    sitting on the personal hygiene device, and
    using the personal hygiene device for douching, irrigating hemorrhoids, performing an enema, or as a bidet, wherein:
      the circumference of said tubular body has an oval shape, and
      the circumference of said tubular body conforms to a circumference of said platform.

12. The method of claim 10, wherein:
    said spray member is selectively removable from said tubular body,
    the second end of said spray member comprises a plurality of openings, and
    said plurality of openings are exposed to the channel in said spray member.

13. The method of claim 10, further comprising a valve operatively connected to said spray member, whereby said valve can be selectively operated to open or close the channel in said spray member.

14. The method of claim 10, wherein:
an adjusting means is operatively connected to said tubular body, said adjusting means comprising:
a mechanism that is selectively operable to adjust an amount of the material in said cavity that flows from said cavity to the channel in said spray member,
an inlet operably connected to said mechanism that allows the material in said cavity to flow into said mechanism, and
an outlet operably connected to said mechanism and operatively connected to said channel at the first end of said spray member, wherein
said outlet allows the material flowing into said mechanism to flow from said mechanism to said channel; and
selectively operating said mechanism to adjust an amount of the material in said cavity that flows from said inlet to said outlet.

15. The method of claim 14, wherein:
said adjusting means comprises a pin that obstructs the material that flows from said inlet to said outlet,
said inlet comprises an inlet tube with a first end and a second end, wherein the first end of said inlet tube is connected to said adjusting means and the second end of said inlet tube extends into the cavity in said tubular body,
said outlet comprises an outlet tube with a first end and a second end,
wherein the first end of said outlet tube is connected to said adjusting means and the second end of said outlet tube is connected to the channel in said spray member; and
selectively adjusting an amount of material that flows from said inlet to said outlet by operating said adjusting means to vary the obstruction by said pin of the material flowing from said inlet to said outlet.

16. The method of claim 10, further comprising a detachable member operatively connected to said spray member at the second end of said spray member, wherein:
said detachable member is selectively attachable and selectively detachable from the second end of said spray member;
said detachable member has an opening; and
said opening in the detachable member is exposed to the channel in said spray member.

17. A personal hygiene device for irrigating a part of a user's body, comprising:
a tubular body, said tubular body having a predetermined shape, a top, and a bottom;
said tubular body constructed of a substantially watertight flexible material;
said tubular body defining a cavity, said cavity having a shape substantially similar to the shape of said tubular body;
an indentation at the bottom of said tubular body, wherein
said indentation runs throughout the bottom of said tubular body;
said indentation has an inner edge and an outer edge; and
said inner edge and said outer edge each have a concave cross section that is similar to each other;
an opening means operatively implemented in said tubular body, said opening means selectively operable to access the cavity in said tubular body and to create a substantially watertight seal in said tubular body at said opening means;
a spray member having an elongated shape, a first end, and a second end, said spray member operatively connected to said tubular body at said first end;
a channel in said spray member, said channel extending from the first end to the second end of said spray member, said channel exposed to the cavity in said tubular body at the first end of said spray member;
an opening in the second end of said spray member, said opening exposed to said channel at the second end of said spray member;
an adjusting means operatively connected to said tubular body, said adjusting means operatively connected to said channel at the first end of said spray member, wherein:
a material contained in the cavity of said tubular body is flowable from said cavity to the channel in said spray member, and
said adjusting means is selectively operable to control the flow of the material in the cavity to the channel in said spray member; and
a detachable member operatively connected to said spray member at said second end, wherein
said detachable member has more than two openings disposed adjacently relative to each other.

18. The personal hygiene device for irrigating a part of a user's body of claim 17, wherein:
said detachable member is selectively attachable and selectively detachable from the second end of said spray member; and
the material in the cavity of said tubular device is a liquid comprising water; and
said tubular body is a toroid having an oval shape.

* * * * *